(12) United States Patent
Kil et al.

(10) Patent No.: US 11,380,932 B2
(45) Date of Patent: Jul. 5, 2022

(54) ELECTROLYTE FOR LITHIUM SECONDARY BATTERIES WITH IMPROVED LOW TEMPERATURE PERFORMANCE AND LITHIUM SECONDARY BATTERY INCLUDING THE SAME

(71) Applicant: LG Chem, Ltd., Seoul (KR)

(72) Inventors: Eun Hye Kil, Daejeon (KR); Jin Kyu Lee, Daejeon (KR); Ki Tae Kim, Daejeon (KR); Hyung Ku Yun, Daejeon (KR); Hyeaeun Han, Daejeon (KR)

(73) Assignee: LG Energy Solution, Ltd.

( * ) Notice: Subject to any disclaimer, the term of this patent is extended or adjusted under 35 U.S.C. 154(b) by 151 days.

(21) Appl. No.: 16/720,300

(22) Filed: Dec. 19, 2019

(65) Prior Publication Data

US 2020/0127319 A1    Apr. 23, 2020

Related U.S. Application Data

(63) Continuation of application No. 15/509,661, filed as application No. PCT/KR2015/013030 on Dec. 2, 2015, now Pat. No. 10,573,921.

(30) Foreign Application Priority Data

Dec. 2, 2014 (KR) .......................... 10-2014-0170329

(51) Int. Cl.
  *H01M 10/052* (2010.01)
  *H01M 10/056* (2010.01)
  (Continued)

(52) U.S. Cl.
  CPC .......... *H01M 10/052* (2013.01); *C07C 69/22* (2013.01); *C07D 317/36* (2013.01); *H01M 4/364* (2013.01);
  (Continued)

(58) Field of Classification Search
  CPC .......... H01M 10/052; H01M 10/0525; H01M 10/056; H01M 10/0566; H01M 10/0569;
  (Continued)

(56) References Cited

U.S. PATENT DOCUMENTS 9,653,754 B2 * 5/2017 Kato ..................... H01M 4/133
9,780,409 B2 * 10/2017 Takiguchi ......... H01M 10/0525
(Continued)

FOREIGN PATENT DOCUMENTS

CN    1346158 A     4/2002
CN    1225045 C    10/2005
(Continued)

OTHER PUBLICATIONS

International Search Report issued in PCT/KR2015/013030 (PCT/ISA/210), dated Mar. 9, 2016.
(Continued)

*Primary Examiner* — Amanda C. Walke
(74) *Attorney, Agent, or Firm* — Lerner, David, Littenberg, Krumholz & Mentlik, LLP

(57) ABSTRACT

Disclosed are an electrolyte for lithium secondary batteries including 10 to 50% by weight of a cyclic carbonate compound, and 50 to 90% by weight of a linear ester compound, based on the total weight of a non-aqueous solvent, wherein a content of ethyl propionate of the linear ester compound is 20 to 60% by weight, based on the total weight of the non-aqueous solvent, and a lithium secondary battery including the electrolyte and exhibiting superior low-temperature characteristics.

16 Claims, 1 Drawing Sheet

(51) Int. Cl.
*H01M 10/0525* (2010.01)
*H01M 10/0566* (2010.01)
*H01M 10/0569* (2010.01)
*H01M 4/525* (2010.01)
*H01M 4/36* (2006.01)
*H01M 4/58* (2010.01)
*C07C 69/22* (2006.01)
*C07D 317/36* (2006.01)

(52) U.S. Cl.
CPC ......... *H01M 4/525* (2013.01); *H01M 4/5825* (2013.01); *H01M 10/056* (2013.01); *H01M 10/0525* (2013.01); *H01M 10/0566* (2013.01); *H01M 10/0569* (2013.01); *H01M 2220/20* (2013.01); *H01M 2300/0037* (2013.01); *Y02E 60/10* (2013.01); *Y02T 10/70* (2013.01)

(58) Field of Classification Search
CPC .... H01M 4/364; H01M 4/525; H01M 4/5825; H01M 2220/20; H01M 2300/0037; C07C 69/22; C07D 317/36
See application file for complete search history.

(56) References Cited

U.S. PATENT DOCUMENTS

| | | | |
|---|---|---|---|
| 9,806,375 B2 * | 10/2017 | Yoshida | H01M 10/056 |
| 9,825,327 B2 * | 11/2017 | Jeon | H01M 10/0567 |
| 9,972,866 B2 * | 5/2018 | Roy | H01M 4/366 |
| 10,665,903 B2 * | 5/2020 | Ihara | H01M 10/0568 |
| 10,763,546 B2 * | 9/2020 | Wang | H01M 4/583 |
| 2002/0076486 A1 | 6/2002 | Kweon et al. | |
| 2002/0142225 A1 | 10/2002 | Kweon et al. | |
| 2006/0154116 A1 | 7/2006 | Siret et al. | |
| 2010/0266904 A1 | 10/2010 | Jeon et al. | |
| 2010/0266905 A1 | 10/2010 | Jeon et al. | |
| 2010/0273064 A1 | 10/2010 | Jeon et al. | |
| 2010/0279168 A1 | 11/2010 | Lee et al. | |
| 2013/0295468 A1 | 11/2013 | Yu et al. | |
| 2014/0011098 A1 | 1/2014 | Jeon et al. | |
| 2015/0004475 A1 | 1/2015 | Jeon et al. | |
| 2015/0017515 A1 | 1/2015 | Jeon et al. | |
| 2015/0086878 A1 | 3/2015 | Yu et al. | |
| 2015/0249271 A1 | 9/2015 | Choi et al. | |

FOREIGN PATENT DOCUMENTS

| | | |
|---|---|---|
| CN | 101682079 A | 3/2010 |
| CN | 101803099 A | 8/2010 |
| CN | 101803101 A | 8/2010 |
| CN | 101911370 A | 12/2010 |
| CN | 103688402 A | 3/2014 |
| CN | 104205469 A | 12/2014 |
| CN | 104247136 A | 12/2014 |
| KR | 20000054948 A | 9/2000 |
| KR | 20060016678 A | 2/2006 |
| KR | 20060069270 A | 6/2006 |
| KR | 20100130973 A | 12/2010 |
| KR | 20120012584 A | 2/2012 |
| KR | 20130118809 A | 10/2013 |
| KR | 20140066050 A | 5/2014 |

OTHER PUBLICATIONS

English Translation of KR10-2014-0066050 (Yoon et al.) (Year:2014).

* cited by examiner

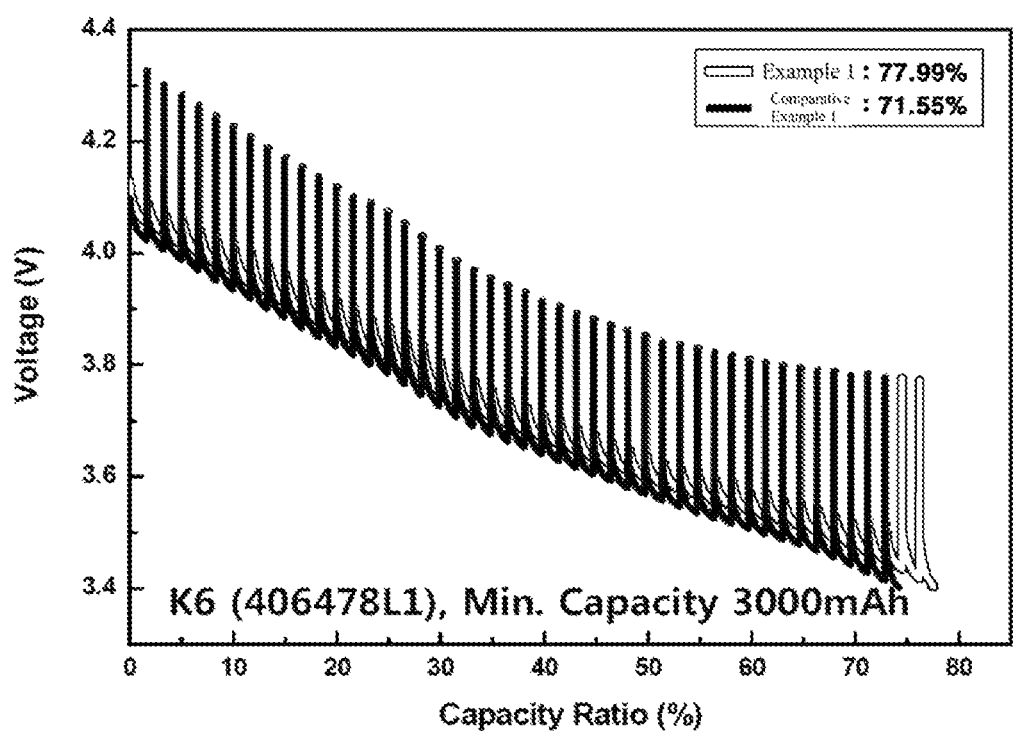

ELECTROLYTE FOR LITHIUM SECONDARY BATTERIES WITH IMPROVED LOW TEMPERATURE PERFORMANCE AND LITHIUM SECONDARY BATTERY INCLUDING THE SAME

CROSS-REFERENCE TO RELATED APPLICATION

This application is a continuation of U.S. patent application Ser. No. 15/509,661, filed on Mar. 8, 2017, which is a national phase entry under 35 U.S.C. § 371 of International Application No. PCT/KR2015/013030 filed Dec. 2, 2015, which claims priority from Korean Patent Application No. 10-2014-0170329 filed Dec. 2, 2014, all of which are incorporated herein by reference.

TECHNICAL FIELD

The present invention relates to an electrolyte for lithium secondary batteries with improved low temperature performance and a lithium secondary battery including the same. More specifically, the present invention relates to an electrolyte for lithium secondary batteries which includes 10 to 50% by weight of a cyclic carbonate compound and 50 to 90% by weight of a linear ester compound, based on the total weight of a non-aqueous solvent to exhibit a predetermined ionic conductivity and viscosity and thus exert improved low temperature performance, and a lithium secondary battery including the same.

BACKGROUND ART

Technological development and increased demand for mobile equipment have led to a rapid increase in the demand for secondary batteries as energy sources. Among secondary batteries, lithium secondary batteries with high energy density and voltage have been commercialized and widely used.

These lithium secondary batteries generally use metal oxides such as lithium cobalt-based oxides, lithium manganese-based oxides, lithium nickel-based oxides and the like as a positive electrode active material, and carbonaceous materials as a negative electrode active material, and such lithium secondary batteries are manufactured by disposing a polyolefin-based porous separator between a negative electrode and a positive electrode and impregnating the resultant structure with a non-aqueous electrolyte containing a lithium salt such as $LiPF_6$ or the like. When the lithium secondary battery is charged, lithium ions of the positive electrode active material are deintercalated and are then intercalated into a carbon layer of the negative electrode. When the lithium secondary battery is discharged, the lithium ions of the carbon layer are deintercalated and are then intercalated into the positive electrode active material. In this regard, the non-aqueous electrolyte acts as a medium through which lithium ions migrate between the negative electrode and the positive electrode.

In particular, such an electrolyte basically requires stability within an operating voltage range of a battery, i.e., 0 to 4.2 V, and high ionic conductivity. The ionic conductivity of an electrolyte is an essential factor determining charge/discharge capacity of batteries, which depends on viscosity of the electrolyte and ion concentrations in the electrolyte. As viscosity of the electrolyte decreases, ions migrate more freely in the electrolyte and ionic conductivity thus increases.

Cyclic carbonate compounds such as ethylene carbonate have a high dielectric constant and play an essential role in realizing battery performance, for example, form an SEI layer during charge/discharge, but have a melting point equal to or higher than room temperature and thus have disadvantages of deteriorated ionic conductivity, high viscosity and poor wettability at low temperature. To solve these disadvantages, a linear carbonate compound such as dimethyl carbonate, ethylmethyl carbonate, diethyl carbonate or the like or a propionate compound, which has a low viscosity, is suitably used in combination.

However, through such solvent composition change alone, it is difficult to improve ionic conductivity of an electrolyte at a low temperature of −10° C., internal resistance increases and discharge characteristics are rapidly deteriorated upon high-rate discharge. Therefore, a variety of research is underway to improve low-temperature characteristics of batteries by suitably controlling the composition and mix ratio of a variety of solvents.

DISCLOSURE

Technical Problem

Therefore, it is one object of the present invention to provide an electrolyte for lithium secondary batteries which includes a predetermined cyclic carbonate compound and a predetermined linear ester compound in a certain mix ratio to offer high ionic conductivity and low viscosity at low temperature.

It is another object of the present invention to provide a lithium secondary battery which includes the electrolyte for lithium secondary batteries to exert superior low-temperature characteristics.

Technical Solution

In accordance with one aspect of the present invention, provided is an electrolyte for lithium secondary batteries including a non-aqueous solvent and a lithium salt, wherein the electrolyte includes 10 to 50% by weight of a cyclic carbonate compound and 50 to 90% by weight of a linear ester compound, based on the total weight of the non-aqueous solvent and a content of ethyl propionate of the linear ester compound is 20 to 60% by weight, based on the total weight of the non-aqueous solvent.

During charging, lithium ions of the positive electrode active material are deintercalated, move to the negative electrode through the electrolyte and are reduced and are then intercalated into a carbon layer of the negative electrode active material. This is greatly affected by ionic conductivity of the electrolyte. When a high-viscosity electrolyte is used, movement of lithium ions is not easy and lithium ions which fail to be intercalated into the negative electrode are deposited in the form of lithium salts on the negative electrode surface, thus causing great deterioration in performance and safety of batteries.

A cyclic carbonate compound has a high dielectric constant and plays an important role in forming a negative electrode protection film (SEI), thus being used as an indispensable ingredient of an electrolyte solvent. However, when taking into consideration the property that the cyclic carbonate compound has low viscosity at low temperature due to high melting point thereof, excessively high content of cyclic carbonate compound may deteriorate rate characteristics and the like.

Accordingly, as described below, the electrolyte according to the present invention includes a cyclic carbonate compound and a linear ester compound under suitably controlled composition and mix ratio conditions, to reduce the viscosity of the electrolyte and, in particular, includes ethyl propionate within a predetermined range to enhance ionic conductivity at low temperature.

Non-limiting examples of the cyclic carbonate compound include one or more selected from the group consisting of ethylene carbonate, 1,2-butylene carbonate, 2,3-butylene carbonate, 1,2-pentylene carbonate, 2,3-pentylene carbonate, fluoroethylene carbonate and vinylene carbonate. Specifically, the cyclic carbonate compound may be ethylene carbonate having a high dielectric constant.

The linear ester compound includes ethyl propionate and non-limiting examples thereof may further include one or more selected from the group consisting of methyl propionate, propyl propionate and butyl propionate.

That is, the electrolyte according to the present invention should include ethyl propionate having a low melting point as a linear ester compound and the electrolyte may, specifically, be a mixture of ethyl propionate and propyl propionate having a low melting point, similar to ethyl propionate.

That is, the electrolyte according to the present invention specifically includes ethylene carbonate having a high dielectric constant and further includes a mixture of ethyl propionate having a melting point of −73.6° C. and propyl propionate, thereby reducing viscosity. In particular, flowability of the electrolyte increases at low temperature, leading to improvement in ionic conductivity and electrochemical performance such as rate characteristics.

Specifically, the electrolyte may include 20 to 40% by weight of ethyl propionate and 20 to 60% by weight of propyl propionate, based on the total weight of the non-aqueous solvent.

Ethyl propionate has a viscosity of about 0.43 cP at room temperature, while propyl propionate has a viscosity of about 0.7 cP at room temperature. According to the mix ratio therebetween, the total viscosity of the electrolyte can be changed. Accordingly, the mix ratio should be determined within the range defined above.

Accordingly, more specifically, the electrolyte may include 25 to 35% by weight of ethyl propionate (EP) and 30 to 40% by weight of propyl propionate (PP), based on the total weight of the non-aqueous solvent.

Meanwhile, when the content of the cyclic carbonate compound is lower than 10% by weight, based on the total weight of the electrolyte, or the content of the linear ester compound is higher than 90% by weight, based on the total weight of the electrolyte, negative electrode protection films (SEI) may not be formed well and lifespan characteristics may thus be rapidly deteriorated. When the content of the cyclic carbonate compound exceeds 50% by weight or the content of the linear ester compound is lower than 50% by weight, disadvantageously, ionic conductivity is lowered, viscosity is increased and rate characteristics are thus deteriorated.

Accordingly, specifically, the electrolyte may include 20 to 40% by weight of a cyclic carbonate compound and 60 to 80% by weight of a linear ester compound, based on the total weight of the electrolyte.

Meanwhile, the electrolyte according to the present invention has the composition described above, thereby having an ionic conductivity equal to or higher than 6.0 mS/cm and equal to or lower than 6.5 mS/cm to at −10° C., and a viscosity at −10° C. equal to or higher than 4.0 cP and equal to or lower than 5.9 cP.

More specifically, the electrolyte may have an ionic conductivity at −10° C. equal to or higher than 5.5 mS/cm and equal to or lower than 6.0 mS/cm and a viscosity at −10° C. equal to or higher than 5.0 cP and equal to or lower than 5.9 cP.

Viscosity may excessively increase at a low temperature such as a temperature lower than −10° C. and ionic conductivity may thus be deteriorated. The present inventors found that, when ionic conductivity at −10° C. is 5.5 mS/cm or more, superior low-temperature characteristics are exerted.

Meanwhile, as temperature increases, flowability of the electrolyte is improved, ionic conductivity is improved and viscosity is deteriorated. The ionic conductivity at −3° C. may be equal to or higher than 5.8 mS/cm and may be equal to or lower than 6.5 mS/cm and ionic conductivity at 0° C. may be equal to or higher than 6.7 mS/cm and may be equal to or lower than 7.5 mS/cm.

In addition, ionic conductivity at 25° C. may be equal to or higher than 8.8 mS/cm and may be equal to or lower than 9.9 mS/cm and viscosity at 25° C. may be equal to or higher than 2.4 cP and may be equal to or lower than 2.8 cP.

The present invention provides a lithium secondary battery including the electrolyte, a positive electrode, a negative electrode and a polymer membrane wherein an electrode assembly having a structure in which the polymer membrane is interposed between the positive electrode and the negative electrode is impregnated with the electrolyte and accommodated in a battery case.

The positive electrode may include, as a positive electrode active material, at least one selected from the group consisting of a compound represented by the following Formula 1 and a compound represented by the following Formula 2.

$$Li_xMO_{2-z}A_z \qquad (1)$$

$$Li_aM'(PO_{4-c})X_c \qquad (2)$$

wherein $0.9 \leq x \leq 1.2$, $0 \leq z < 0.2$, $0.5 \leq a \leq 1.5$, $0 \leq c \leq 0.1$;

M includes at least one element selected from the group consisting of Co, Ni, Mn, Al, Mg, Fe, Cr, V, Ti, Cu, B, Ca, Zn, Zr, Nb, Mo, Sr, Sb, W, Ti and Bi;

M' includes at least one element selected from the group consisting of Fe, Mn, Co, Ni, Cu, Zn, Mg, Cr, V, Mo, Ti, Al, Nb, B, and Ga;

A includes at least one anion with a charge of −1 or −2; and

X includes at least one element selected from F, S and N.

Specifically, the compound represented by Formula 1 may be represented by the following Formula 3 and the compound represented by Formula 2 may be represented by the following Formula 4.

$$Li_xCo_yM_{1-y}O_{2-z}A_z \qquad (3)$$

$$Li_aFe_{1-b}M'_b(PO_{4-c})X_c \qquad (4)$$

wherein $0.9 \leq x \leq 1.2$, $0 < y \leq 1$, $0 \leq z < 0.2$, $0.5 \leq a \leq 1.5$, $0 \leq b \leq 0.5$, $0 \leq c \leq 0.1$;

M includes at least one element selected from the group consisting of Ni, Mn, Al, Mg, Fe, Cr, V, Ti, Cu, B, Ca, Zn, Zr, Nb, Mo, Sr, Sb, W, Ti and Bi;

M' includes at least one element selected from the group consisting of Mn, Co, Ni, Cu, Zn, Mg, Cr, V, Mo, Ti, Al, Nb, B, and Ga;

A includes at least one anion with a charge of −1 or −2; and

X includes at least one element selected from F, S and N.

More specifically, the compound represented by Formula 3 may include at least one selected from the group consisting of $LiCoO_2$, $LiNiO_2$, $LiMnO_2$, $LiNi_{0.5}Mn_{0.3}Co_{0.2}O_2$, $LiNi_{0.4}Mn_{0.4}Co_{0.2}O_2$, and $LiNi_{1/3}Co_{1/3}Mn_{1/3}O_2$, specifically $LCoO_2$.

The compound represented by Formula 4 may be $LiFePO_4$.

The positive electrode active material may include the compound of Formula 1, or the compound of Formula 2, or the compounds of Formulae 1 and 2.

Specifically, the positive electrode active material according to the present invention may be $LiCoO_2$, or $LiFePO_4$. In some cases, $LiCoO_2$ may be used in combination with $LiFePO_4$ to prevent rapid power drop resulting from a resistance increase within a certain voltage range.

When the positive electrode active material includes the compound of Formula 1 and the compound of Formula 2, a mix ratio, on a weight basis, of the compound of Formula 1 and the compound of Formula 2 may be 60:40 to 99:1, specifically 70:30 to 99:1.

Disadvantageously, when the content of the compound of Formula 1 is excessively low or the content of the compound of Formula 2 is excessively high, it may be difficult to increase capacity and energy of batteries and, when the content of the compound of Formula 1 is excessively high or the content of the compound of Formula 2 is excessively low, in a certain range, the compound of Formula 2 cannot effectively assist output of the compound of Formula 1.

In order to improve safety of the positive electrode active material, the present invention may further include a compound represented by $Li_xM''_yMn_{2-y'}O_{4-z'}A_{z'}$, (wherein $0.9 \le x' \le 1.2$, $0 \le y' < 2$, $0 \le z' < 0.2$, M" includes at least one element selected from the group consisting of Al, Mg, Ni, Co, Fe, Cr, V, Ti, Cu, B, Ca, Zn, Zr, Nb, Mo, Sr, Sb, W, Ti and Bi, and A includes at least one anion with a charge of $-1$ or $-2$), specifically 1 to 20% of at least one selected from the group consisting of $LiNi_{0.5}Mn_{1.5}O_4$, $LiNi_{0.4}Mn_{1.6}O_4$, and $LiMn_2O_4$ with respect to the total weight of the positive electrode active material.

The negative electrode may include, as a negative electrode active material, a carbon-based material.

Any carbon-based material may be used without limitation so long as it includes carbon. For example, the carbon-based material may be crystalline carbon such as natural graphite and artificial graphite, or amorphous carbon such as soft carbon and hard carbon and the carbon-based material may specifically be artificial graphite.

In addition, if necessary, the negative electrode active material may further include metal composite oxides such as $Li_xFe_2O_3 (0 \le x \le 1)$, $Li_xWO_2 (0 \le x \le 1)$, and $Au_xMe_{1-x}Me'_yO_z$ (Me: Mn, Fe, Pb, Ge; Me': Al, B, P, Si, Group I, Group II, and Group III elements, halogens; $0 < x \le 1$; $1 \le y \le 3$; $1 \le z \le 8$); lithium metals; lithium alloys; silicon-based alloys; tin-based alloys; metal oxides such as $AuO$, $SnO_2$, $PbO$, $PbO_2$, $Pb_2O_3$, $Pb_3O_4$, $Sb_2O_3$, $Sb_2O_4$, $Sb_2O_5$, $GeO$, $GeO_2$, $Bi_2O_3$, $Bi_2O_4$, and $Bi_2O_5$; conductive polymers such as polyacetylene; Li—Co—Ni-based materials; titanium oxides; lithium titanium oxides and the like, in an amount of 1 to 20%, with respect to the total weight of the negative electrode active material.

The positive electrode is produced by applying a mixture of the positive electrode active material, a conductive material and a binder to a positive electrode current collector, followed by drying and pressing. The negative electrode is also produced in the same manner as the positive electrode and the mixture may further include a filler, if necessary.

The positive electrode current collector is generally produced to have a thickness of 3 to 500 µm. There is no particular limit as to the positive electrode current collector, so long as it has high conductivity without causing adverse chemical changes in the fabricated battery. Examples of the positive electrode current collector include stainless steel, aluminum, nickel, titanium, sintered carbon, and aluminum or stainless steel which has been surface-treated with carbon, nickel, titanium, silver or the like. If necessary, the current collector may also be processed to form fine irregularities on the surface thereof so as to enhance adhesion to the positive electrode active material. In addition, the current collector may be used in various forms including films, sheets, foils, nets, porous structures, foams and non-woven fabrics.

The conductive material is typically added in an amount of 1 to 50% by weight, based on the total weight of the mixture including the positive electrode active material. Any conductive material may be used without particular limitation so long as it has suitable conductivity without causing adverse chemical changes in the battery. Examples of suitable conductive materials include graphite such as natural graphite and artificial graphite; carbon blacks such as carbon black, acetylene black, Ketjen black, channel black, furnace black, lamp black and thermal black; conductive fibers such as carbon fibers and metallic fibers; metallic powders such as carbon fluoride powders, aluminum powders and nickel powders; conductive whiskers such as zinc oxide and potassium titanate; conductive metal oxides such as titanium oxide; and polyphenylene derivatives.

The binder is a component assisting in binding between an active material and a conductive material and in binding of the active material to a current collector. The binder is typically added in an amount of 1 to 50% by weight, with respect to the total weight of the mixture including the positive electrode active material. Examples of the binder include polyvinylidene fluoride, polyvinyl alcohol, carboxymethylcellulose (CMC), starch, hydroxypropylcellulose, regenerated cellulose, polyvinyl pyrrolidone, tetrafluoroethylene, polyethylene, polypropylene, ethylene propylene diene terpolymer (EPDM), sulfonated EPDM, styrene butadiene rubber, fluororubbers and various copolymers.

The filler may be optionally added to suppress expansion of the positive electrode. Any filler may be used without particular limitation so long as it does not cause adverse chemical changes in the manufactured battery and is a fibrous material. Examples of the filler include olefin polymers such as polyethylene and polypropylene; and fibrous materials such as glass fibers and carbon fibers.

The negative electrode current collector is generally produced to have a thickness of 3 to 500 µm. There is no particular limit as to the negative electrode current collector, so long as it has suitable conductivity without causing adverse chemical changes in the fabricated battery. Examples of the negative electrode current collector include copper, stainless steel, aluminum, nickel, titanium, sintered carbon, and copper or stainless steel which has been surface-treated with carbon, nickel, titanium, silver or the like, and aluminum-cadmium alloys. Similar to the positive electrode current collector, if necessary, the negative electrode current collector may be processed to form fine irregularities on the surface thereof so as to enhance adhesion to the negative electrode active material. In addition, the current collector may be used in various forms including films, sheets, foils, nets, porous structures, foams and non-woven fabrics.

Such a lithium secondary battery may have a structure in which an electrode assembly having a structure in which the polymer membrane is disposed between the positive electrode and the negative electrode is impregnated with the electrolyte for lithium secondary batteries containing a non-aqueous solvent and a lithium salt, as defined above.

The separator is interposed between the positive electrode and the negative electrode. As the separator, an insulating thin film having high ion permeability and mechanical strength is used. The separator typically has a pore diameter of 0.01 to 10 μm and a thickness of 5 to 300 μm. As the separator, sheets or non-woven fabrics, made of an olefin polymer such as polypropylene and/or glass fibers or polyethylene, which have chemical resistance and hydrophobicity, are used. When a solid electrolyte such as a polymer is employed as the electrolyte, the solid electrolyte may also serve as both the separator and the electrolyte.

The lithium salt-containing non-aqueous electrolyte is composed of a non-aqueous electrolyte and a lithium salt, as described above.

The lithium salt is a material that is readily soluble in the above-mentioned non-aqueous electrolyte and may include, for example, LiCl, LiBr, LiI, $LiClO_4$, $LiBF_4$, $LiB_{10}Cl_{10}$, $LiPF_6$, $LiCF_3SO_3$, $LiCF_3CO_2$, $LiAsF_6$, $LiSbF_6$, $LiAlCl_4$, $CH_3SO_3Li$, $CF_3SO_3Li$, LiSCN, $LiC(CF_3SO_2)_3$, $(CF_3SO_2)_2NLi$, chloroborane lithium, lower aliphatic carboxylic acid lithium, lithium tetraphenyl borate and imides.

Additionally, in order to improve charge/discharge characteristics and flame retardancy, for example, pyridine, triethylphosphite, triethanolamine, cyclic ether, ethylenediamine, n-glyme, hexaphosphoric triamide, nitrobenzene derivatives, sulfur, quinone imine dyes, N-substituted oxazolidinone, N,N-substituted imidazolidine, ethylene glycol dialkyl ether, ammonium salts, pyrrole, 2-methoxy ethanol, aluminum trichloride or the like may be added to the non-aqueous electrolyte. If necessary, in order to impart incombustibility, the non-aqueous electrolyte may further include halogen-containing solvents such as carbon tetrachloride and ethylene trifluoride. Further, in order to improve high-temperature storage characteristics, the non-aqueous electrolyte may additionally include carbon dioxide gas and may further contain fluoro-ethylene carbonate (FEC), propene sultone (PRS) and the like.

The present invention also provides a battery pack including the lithium secondary battery as a unit battery.

The battery pack can be used a power source of devices requiring high-temperature stability, long cycle characteristics and high rate characteristics.

Examples of such devices include, but are not limited to, electric motor-driven power tools; electric vehicles (EVs), hybrid electric vehicles (HEVs), and plug-in hybrid electric vehicles (PHEVs); electric two-wheeled vehicles such as e-bikes and e-scooters; electric golf carts; and systems for storing power.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a graph showing low-temperature intermittent discharge testing at 10° C. for Example 2 and Comparative Example 3 in Test Example 2.

BEST MODE

Now, the present invention will be described in more detail with reference to the following examples. These examples are provided only to illustrate the present invention and should not be construed as limiting the scope and spirit of the present invention.

Example 1

An electrolyte for lithium secondary batteries containing 1M $LiPF_6$ dissolved in a mixed solvent including ethylene carbonate (EC), ethyl propionate (EP) and propyl propionate (PP) in a weight mix ratio of 3:3:4 was prepared.

Example 2

An electrolyte for lithium secondary batteries was prepared in the same manner as in Example 1, except that ethylene carbonate (EC), propylene carbonate (PC), ethyl propionate (EP) and propyl propionate (PP) were used in a weight mix ratio of 2.5:1:2.5:4.0 for the electrolyte solvent.

Example 3

An electrolyte for lithium secondary batteries was prepared in the same manner as in Example 1, except that ethylene carbonate (EC), propylene carbonate (PC), ethyl propionate (EP) and propyl propionate (PP) were used in a weight mix ratio of 2.5:0.5:2.5:4.5 for the electrolyte solvent.

Comparative Example 1

An electrolyte for lithium secondary batteries was prepared in the same manner as in Example 1, except that ethylene carbonate (EC), propylene carbonate (PC) and propyl propionate (PP) were used in a weight mix ratio of 3:1:6 for the electrolyte solvent.

The compositions of the electrolytes for lithium secondary batteries according to Examples 1 to 3 and Comparative Example 1 are summarized and shown in the following Table 1.

TABLE 1

|  | EC | PC | EP | PP |
|---|---|---|---|---|
| Example 1 | 30 | 0 | 30 | 40 |
| Example 2 | 25 | 10 | 25 | 40 |
| Example 3 | 25 | 5 | 25 | 45 |
| Comparative Example 1 | 30 | 10 | 0 | 60 |

Test Example 1

The ionic conductivity and viscosity of the electrolytes for lithium secondary batteries according to Examples 1 to 3 and Comparative Example 1 are measured and shown in the following Table 1.

TABLE 2

|  | Ionic Conductivity (mS/cm) | | | | | Viscosity (cP) | |
|---|---|---|---|---|---|---|---|
|  | 25° C. | 10° C. | 0° C. | −3° C. | −10° C. | 25° C. | −10° C. |
| Example 1 | 9.27 | 7.72 | 6.89 | 6.07 | 5.66 | 2.66 | 5.67 |
| Example 2 | 9.42 | 7.74 | 6.87 | 6.01 | 5.57 | 2.71 | 5.99 |
| Example 3 | 8.89 | 7.45 | 6.67 | 5.8 | 5.44 | 2.72 | 5.94 |
| Comparative Example 1 | 8.47 | 6.72 | 5.84 | 5.02 | 4.58 | 3.28 | 8.13 |

As can be seen from Table 2, the electrolytes according to Examples 1 to 3 show significant difference in ionic conductivity and viscosity at −10° C. from the electrolyte according to Comparative Example 1.

Specifically, Examples 1 to 3 exhibit an ionic conductivity of 5.44 mS/cm or more and a viscosity of 5.99 cP or less at −10° C., whereas Comparative Example 1 exhibits ionic conductivity of 4.58 mS/cm and high viscosity of 8.13 cP at −10° C.

In addition, Examples 1 to 3 exhibit a high ionic conductivity and a low viscosity even at 25° C., as compared to Comparative Example 1 and the electrolyte according to the present invention exhibits excellent wetting properties at low temperature as well as at room temperature.

In addition, when comparing linear ester compounds, Examples 1 and 2 include the same amount of PP, Example 3 includes slightly increased amount of PP, and Comparative Example 1 includes only PP, without EP. It can be seen that as PP content increases, ionic conductivity and viscosity are deteriorated.

That is, as to the composition of the electrolyte, as ethyl propionate (EP) proportion increases and propyl propionate (PP) proportion decreases, low temperature performance can be effectively improved. In particular, the electrolyte of Example 1 including 30% by weight of EP and 40% by weight of PP exhibits a 9.5% increase in ionic conductivity at 25° C. and a 18% increase in ionic conductivity at 0° C., and a 2% decrease in viscosity at room temperature and a 40% decrease in viscosity at −10° C., as compared to the electrolyte of Comparative Example 1 including only 70% by weight of PP as a linear ester compound.

Example 4

A negative electrode active material (graphite), a conductive material (Denka black) and a binder (PVdF) were mixed in NMP in a weight ratio of 96.25:1:2.75 to prepare a negative electrode mixture, and a 20 µm thickness copper foil was coated to a thickness of 200 µm with the negative electrode mixture, followed by pressing and drying to fabricate a negative electrode.

In addition, a positive electrode active material composed of $LiCoO_2$ and $LiFePO_4$ (in a weight mix ratio of 97.5:2.5), a conductive material (Denka black) and a binder (PVdF) were mixed in NMP in a weight ratio of 96:2:2, and a 20 µm thickness aluminum foil was coated to a thickness of 200 µm with the formed positive electrode mixture, followed by pressing and drying to fabricate a positive electrode.

As a separation membrane, a polyethylene membrane (Celgard, thickness: 20 µm) was interposed between the negative electrode and the positive electrode, and a lithium secondary battery was produced using the electrolyte for lithium secondary batteries prepared in Example 1.

Comparative Example 2

A lithium secondary battery was produced in the same manner as in Example 4, except that the electrolyte for lithium secondary batteries prepared in Comparative Example 1 was used.

Test Example 2

The secondary batteries of Example 4 and Comparative Example 2 were subjected to low-temperature intermittent discharge testing under the following conditions at −10° C. and results are shown in FIG. 1.

1) Charge: CC (600 mA)-CV (4.35V), 50 mA cut-off
2) Rest: 10 min
3) Discharge: CC (600 mA), 5 min
4) Rest: 20 min
5) Repeat 3) until 3.4V As can be seen from FIG. 1, the battery according to Example 4 uses an electrolyte exhibiting a high ionic conductivity and a low viscosity at low temperature and exhibits a 9% increase in intermittent discharge characteristics at −10° C., as compared to the battery of Comparative Example 2.

INDUSTRIAL APPLICABILITY

As apparent from the fore-going, the electrolyte for secondary batteries according to the present invention includes predetermined cyclic carbonate and linear ester compounds in a certain ratio, and thus has an improved ionic conductivity and a low viscosity, more specifically, ionic conductivity at −10° C. equal to or higher than 5.5 mS/cm and equal to or lower than 6.5 mS/cm, and a viscosity at −10° C., equal to or higher than 4.5 cP and equal to or lower than 5.9 cP. As a result, wettability of the electrolyte can be improved. The lithium secondary battery including the electrolyte can exhibit excellent electrochemical properties such as rate characteristics at low temperature.

The invention claimed is:

1. An electrolyte for lithium secondary batteries, consisting of:
   a non-aqueous solvent, a lithium salt, and an additive that is selected from flame retardants, halogen-containing solvents, carbon dioxide gas, fluoro-ethylene carbonate (FEC), or propene sultone (PRS),
   wherein the non-aqueous solvent consists of 10 to 50% by weight of a cyclic carbonate compound; and
   50 to 90% by weight of a linear ester compound, the linear ester compound is a mixture of ethyl propionate and propyl propionate, and
   the content of ethyl propionate is 20 to 40% by weight, and the content of propyl propionate is 30 to 50% by weight, based on the total weight of the non-aqueous solvent.

2. The electrolyte according to claim 1, wherein the cyclic carbonate compound comprises at least one selected from the group consisting of ethylene carbonate, 1,2-butylene carbonate, 2,3-butylene carbonate, 1,2-pentylene carbonate, 2,3-pentylene carbonate, fluorethylene carbonate and vinylene carbonate.

3. The electrolyte according to claim 2, wherein the cyclic carbonate compound comprises ethylene carbonate.

4. The electrolyte according to claim 1, wherein the non-aqueous solvent consists of 20 to 50% by weight of a cyclic carbonate compound; and
   50 to 80% by weight of a linear ester compound, the linear ester compound is a mixture of ethyl propionate and propyl propionate, and
   the content of ethyl propionate is 20 to 40% by weight, and the content of propyl propionate is 30 to 40% by weight, based on the total weight of the non-aqueous solvent.

5. The electrolyte according to claim 1, wherein, the electrolyte comprises 20 to 40% by weight of the cyclic carbonate compound and 60 to 80% by weight of the linear ester compound, based on the total weight of the non-aqueous solvent.

6. The electrolyte according to claim 1, wherein the electrolyte has an ionic conductivity at −10° C. equal to or higher than 5.5 mS/cm and equal to or lower than 6.5 mS/cm and a viscosity at −10° C. equal to or higher than 4.5 cP and equal to or lower than 5.9 cP.

7. The electrolyte according to claim 1, wherein, the electrolyte has an ionic conductivity at −10° C. equal to or higher than 5.5 mS/cm and equal to or lower than 6.0 mS/cm and a viscosity at −10° C. equal to or higher than 5.0 cP and equal to or lower than 5.9 cP.

8. The electrolyte according to claim 1, wherein the additive is at least one selected from the group consisting of pyridine, triethylphosphite, triethanolamine, cyclic ether, ethylenediamine, n-glyme, hexaphosphoric triamide, nitrobenzene derivatives, sulfur, quinone imine dyes, N-substituted oxazolidinone, N,N-substituted imidazolidine, ethylene glycol dialkyl ether, ammonium salts, pyrrole, 2-methoxy ethanol, aluminum trichloride, carbon tetrachloride and ethylene trifluoride, carbon dioxide gas, fluoroethylene carbonate (FEC), and propene sultone (PRS).

9. A lithium secondary battery comprising:
the electrolyte according to claim 1;
a positive electrode;
a negative electrode; and
a polymer membrane,
wherein an electrode assembly having a structure in which the polymer membrane is interposed between the positive electrode and the negative electrode is impregnated with the electrolyte and accommodated in a battery case.

10. The lithium secondary battery according to claim 9, wherein the positive electrode comprises, as a positive electrode active material, at least one selected from the group consisting of a compound represented by the following Formula 1 and a compound represented by the following Formula 2:

$$Li_xMO_{2-z}A_z \qquad (1)$$

$$Li_aM'(PO_{4-c})X_c \qquad (2)$$

wherein $0.9 \leq x \leq 1.2$, $0 \leq z \leq 0.2$, $0.5 \leq a \leq 1.5$, $0 \leq c \leq 0.1$;

M comprises at least one element selected from the group consisting of Co, Ni, Mn, Al, Mg, Fe, Cr, V, Ti, Cu, B, Ca, Zn, Zr, Nb, Mo, Sr, Sb, W, Ti and Bi;

M' comprises at least one element selected from the group consisting of Fe, Mn, Co, Ni, Cu, An, Mg, Cr, V, Mo, Ti, Al, Nb, B, and Ga;

A comprises at least one anion with a charge of −1 or −2; and

X comprises at least one element selected from F, S and N.

11. The lithium secondary battery according to claim 10, wherein the compound represented by Formula 1 is represented by the following Formula 3 and the compound represented by Formula 2 is represented by the following Formula 4:

$$Li_xCo_yM_{1-y}O_{2-z}A_z \qquad (3)$$

$$Li_aFe_{1-b}M'_b(PO_{4-c})X_c \qquad (4)$$

wherein $0.9 \leq x \leq 1.2$, $0 \leq y \leq 1$, $0 \leq z \leq 0.2$, $0.5 \leq a \leq 1.5$, $0 \leq b \leq 0.5$, $0 \leq c \leq 0.1$;

M comprises at least one element selected from the group consisting of Ni, Mn, Al, Mg, Fe, Cr, V, Ti, Cu, B, Ca, Zn, Zr, Nb, Mo, Sr, Sb, W, Ti and Bi;

M' comprises at least one element selected from the group consisting of Mn, Co, Ni, Cu, Zn, Mg, Cr, V, Mo, Ti, Al, Nb, B, and Ga;

A comprises at least one anion with a charge of −1 or −2; and

X comprises at least one element selected from F, S and N.

12. The lithium secondary battery according to claim 11, wherein the compound represented by Formula 3 is $LCoO_2$ and the compound represented by Formula 4 is $LiFePO_4$.

13. The lithium secondary battery according to claim 10, wherein the positive electrode active material comprises the compound of Formula 1 and the compound of Formula 2, and a weight mix ratio of the compound of Formula 1 and the compound of Formula 2 is 60:40 to 99:1.

14. The lithium secondary battery according to claim 13, wherein the weight mix ratio of the compound of Formula 1 and the compound of Formula 2 is 70:30 to 99:1.

15. The lithium secondary battery according to claim 9, wherein the negative electrode comprises, as a negative electrode active material, a carbon-based material.

16. A battery pack comprising the lithium secondary battery according to claim 9 as a unit battery.

* * * * *